(12) United States Patent
Willis et al.

(10) Patent No.: US 10,987,230 B2
(45) Date of Patent: *Apr. 27, 2021

(54) SPINAL FUSION IMPLANT

(71) Applicant: Stryker European Operations Holdings, LLC, Wilmington, DE (US)

(72) Inventors: Steven Willis, Mahwah, NJ (US); Robert Cipoletti, Pompton Plains, NJ (US)

(73) Assignee: Stryker European Operations Holdings LLC, Kalamazoo, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/459,793

(22) Filed: Jul. 2, 2019

(65) Prior Publication Data

US 2019/0321192 A1   Oct. 24, 2019

Related U.S. Application Data

(63) Continuation of application No. 15/891,612, filed on Feb. 8, 2018, now Pat. No. 10,369,011, which is a continuation of application No. 14/520,849, filed on Oct. 22, 2014, now Pat. No. 9,918,851.

(51) Int. Cl.
*A61F 2/44* (2006.01)
*A61F 2/30* (2006.01)

(52) U.S. Cl.
CPC .......... *A61F 2/447* (2013.01); *A61F 2/4455* (2013.01); *A61F 2002/3008* (2013.01); *A61F 2002/30056* (2013.01); *A61F 2002/3071* (2013.01); *A61F 2002/3082* (2013.01); *A61F 2002/30082* (2013.01); *A61F 2002/30151* (2013.01); *A61F 2002/30156* (2013.01); *A61F 2002/30777* (2013.01); *A61F 2002/30823* (2013.01); *A61F 2002/30884* (2013.01); *A61F 2002/30891* (2013.01); *A61F 2002/30904* (2013.01); *A61F 2310/00011* (2013.01)

(58) Field of Classification Search
CPC .............. A61F 2/4425; A61F 2002/443; A61F 2/4455; A61F 2/447; A61F 2002/4475; A61F 2/4611
See application file for complete search history.

(56) References Cited

U.S. PATENT DOCUMENTS

| | | |
|---|---|---|
| 5,562,736 A | 10/1996 | Ray et al. |
| 5,676,146 A | 10/1997 | Scarborough |
| 5,860,973 A | 1/1999 | Michelson |

(Continued)

FOREIGN PATENT DOCUMENTS

| | | |
|---|---|---|
| EP | 1384455 A1 | 1/2004 |
| WO | 9640014 A1 | 12/1996 |

OTHER PUBLICATIONS

Extended European Search Report for Application No. EP15191120 dated Mar. 14, 2016.

*Primary Examiner* — Julianna N Harvey
(74) *Attorney, Agent, or Firm* — Lerner, David, Littenberg, Krumholz & Mentlik, LLP

(57) ABSTRACT

A spinal fusion implant including a body and a jacket is disclosed. The jacket includes at least two radiopaque markers extending therefrom for use in determining the position of the implant after placement between intervertebral bodies. Methods of implanting and evaluating positioning of the implant are also disclosed.

20 Claims, 14 Drawing Sheets

(56) References Cited

U.S. PATENT DOCUMENTS

| | | |
|---|---|---|
| 7,060,073 B2 | 6/2006 | Frey et al. |
| 7,918,891 B1 | 4/2011 | Curran et al. |
| 8,083,796 B1 | 12/2011 | Raiszadeh et al. |
| 8,187,334 B2 | 5/2012 | Curran et al. |
| 8,246,686 B1 | 8/2012 | Curran et al. |
| 8,349,015 B2 | 1/2013 | Bae et al. |
| 8,361,156 B2 | 1/2013 | Curran et al. |
| 8,574,301 B2 | 11/2013 | Curran et al. |
| 8,585,105 B1 | 11/2013 | Dobbins, Sr. |
| 8,608,804 B2 | 12/2013 | Curran et al. |
| 8,814,940 B2 | 8/2014 | Curran et al. |
| 2003/0135275 A1* | 7/2003 | Garcia .................. A61F 2/4611 623/17.11 |
| 2004/0019356 A1* | 1/2004 | Fraser .................. A61F 2/4684 606/102 |
| 2005/0010290 A1 | 1/2005 | Hawkins |
| 2006/0074488 A1 | 4/2006 | Abdou |
| 2007/0093898 A1 | 4/2007 | Schwab et al. |
| 2010/0121436 A1* | 5/2010 | Tuval ..................... A61B 34/20 623/2.17 |
| 2010/0204737 A1 | 8/2010 | Bae et al. |
| 2011/0112642 A1* | 5/2011 | Tohmeh ................ A61F 2/4455 623/17.11 |
| 2011/0282395 A1* | 11/2011 | Beyar ..................... A61B 17/80 606/301 |
| 2012/0065733 A1* | 3/2012 | Wieder ................ A61F 2/4455 623/17.11 |
| 2012/0101582 A1* | 4/2012 | Raiszadeh ............... A61F 2/442 623/17.16 |
| 2012/0209388 A1* | 8/2012 | Curran .................... A61F 2/442 623/17.16 |
| 2014/0309742 A1 | 10/2014 | Curran et al. |

* cited by examiner

SPINAL FUSION IMPLANT

CROSS-REFERENCE TO RELATED APPLICATIONS

This application is a continuation of U.S. application Ser. No. 15/891,612, filed on Feb. 8, 2018, which is a continuation of U.S. application Ser. No. 14/520,849, filed on Oct. 22, 2014, the disclosures of which are incorporated herein by reference.

BACKGROUND OF THE INVENTION

The present invention relates to spinal surgery, namely, the fusion of adjacent intervertebral bodies.

Back pain can be caused by many different maladies, not the least of which are problems that directly impact the intervertebral disks of the spine. Typical disc issues include, inter alia, degeneration, bulging, herniation, thinning and abnormal movement. One method of treatment of such disc problems that has been widely utilized in the field of spinal surgery is a spinal fusion procedure, whereby an affected disc is removed, and the adjacent vertebral bodies are fused together. Currently, implants, pedicle screws and the like are utilized to facilitate the fusion.

One type of implant that has recently gained favor are so-called stand-alone cages. These intervertebral implants effectuate spinal fusion without the need for secondary fixation through the use of, for instance, pedicle screws. One example of such a stand-alone cage is disclosed in U.S. Pat. No. 8,349,015 ("the '015 patent"), the disclosure of which is hereby incorporated by reference herein. In the '015 patent, a PEEK body is surrounded by a metallic jacket and anchors are inserted through both superior and inferior surfaces the implant and into the upper and lower adjacent vertebral bodies respectively.

Although stand-alone cages are successful in effectuating spine fusion, intraoperative and postoperative visualization of the implants remains a challenge. This is especially true given the advent of polymeric implants that are constructed of PEEK and therefore do not show up when conducting standard imaging processes. Nonetheless, surgeons typically need to verify proper implant position, location and rotation.

It has been known for some time to imbed radiopaque markers in polymeric bodies, so that at least the markers show up on X-rays or other images taken of the implant. Surgeon can compare the positions of the markers to each other and/or the anatomical features of the spine to determine whether the implant is properly placed. However, implants with such a design require additional manufacturing efforts (i.e., imbedding the markers in the polymeric) that are costly, time consuming and may adversely affect the structural integrity of the implants.

Therefore, there exists a need for an improved spinal implant that overcomes the aforementioned drawbacks.

BRIEF SUMMARY OF THE INVENTION

The present invention provides a unique design that allows for evaluation of the placement of a spinal fusion implant. In its most basic sense, the invention includes at least two extensions extending from a jacket surrounding an implant body that are radiopaque. These extensions can be viewed via an imaging technique and their orientation with respect to each other or other aspects of the implant can aid a surgeon in determining whether the implant is properly placed. Of course, the specific configuration of the extensions may widely vary, as can the specific implants themselves.

A first aspect of the present invention is an intervertebral implant including a body sized and shaped for placement between first and second adjacent vertebrae, a jacket disposed around the spacer and at least two radiopaque markers extending from the jacket to enable identification of an orientation of the implant.

In certain embodiments of the first aspect, the implant may further include first and second anchors secured to the implant and the first and second vertebrae. The at least two radiopaque markers may be located on opposite sides of the jacket. In an aligned orientation, only one of the at least two markers is visible from a first aspect, and when the implant is in a misaligned orientation portions of both of the at least two markers are visible from the first aspect. The body may be at least partially radiolucent. The at least two radiopaque markers may include four radiopaque markers, and the four radiopaque markers may be angled with respect to upper and lower surfaces of the implant. The jacket may include two rails and the at least two radiopaque markers may extend between the rails. The at least two radioapque markers may be triangular.

Another aspect of the present invention is a method of determining the orientation of an implant placed between two intervertebral bodies including the steps of viewing opposed radioactive markers located on front and back sides of a jacket of the implant and determining the orientation of the implant based on the orientation of the markers. In an aligned orientation, only a single marker is visible from a first aspect. In a misaligned orientation, at least portions of each of the markers are visible from the first aspect. The first aspect may be from an anterior side of a patient.

Another aspect of the present invention is a method of implanting an implant between two intervertebral bodies including the steps of accessing the space between the intervertebral bodies, placing the implant between the intervertebral bodies, viewing opposed radioactive markers located on front and back sides of a jacket of the implant; and determining the orientation of the implant based on the orientation of the markers. In an aligned orientation, only a single marker may be visible from a first aspect. In a misaligned orientation, at least portions of each of the markers may be visible from the first aspect. The first aspect may from an anterior side of a patient.

BRIEF DESCRIPTION OF THE DRAWINGS

A more complete appreciation of the subject matter of the present invention and of the various advantages thereof can be realized by reference to the following detailed description in which reference is made to the accompanying drawings in which.

DETAILED DESCRIPTION

Figure 1:
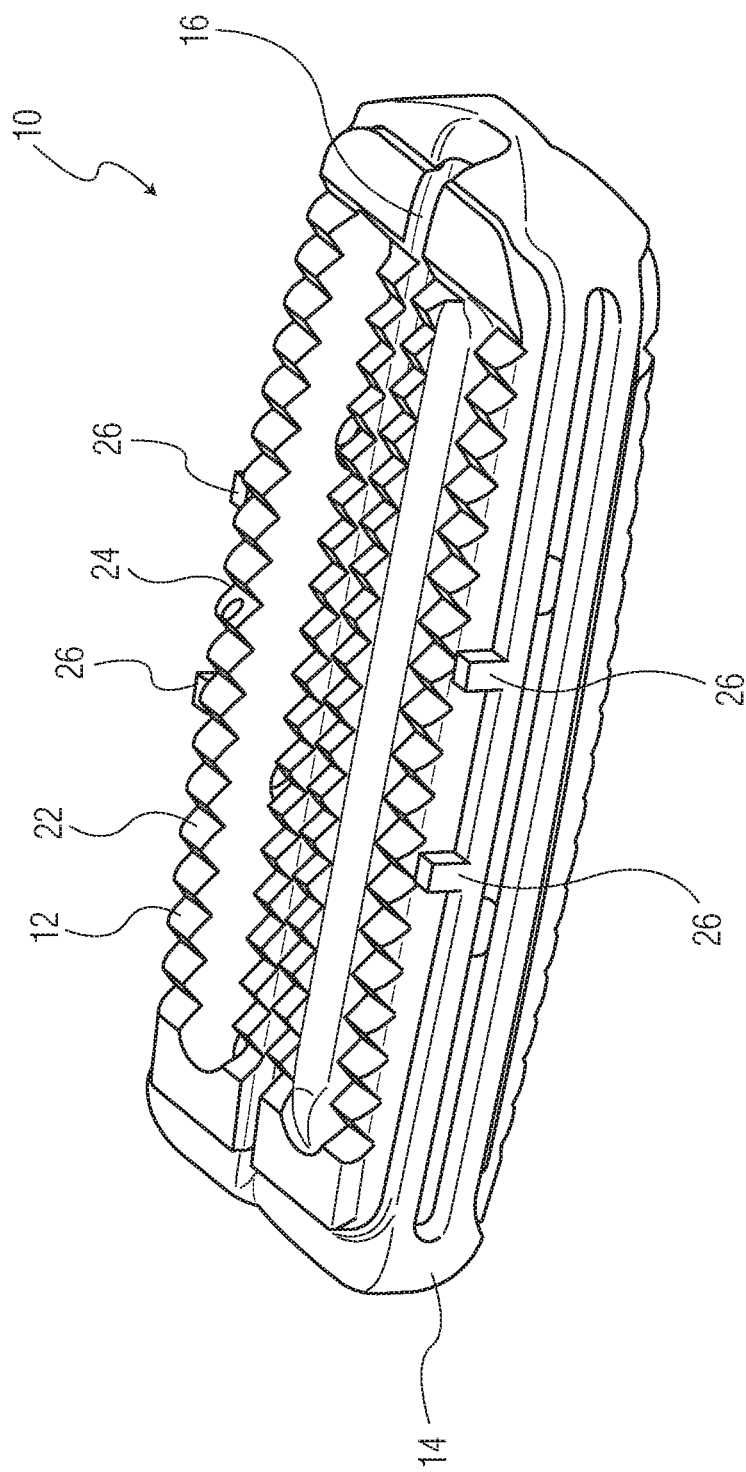
FIG. 1 is a perspective view of an implant according to one embodiment of the present invention.
Figure 2:
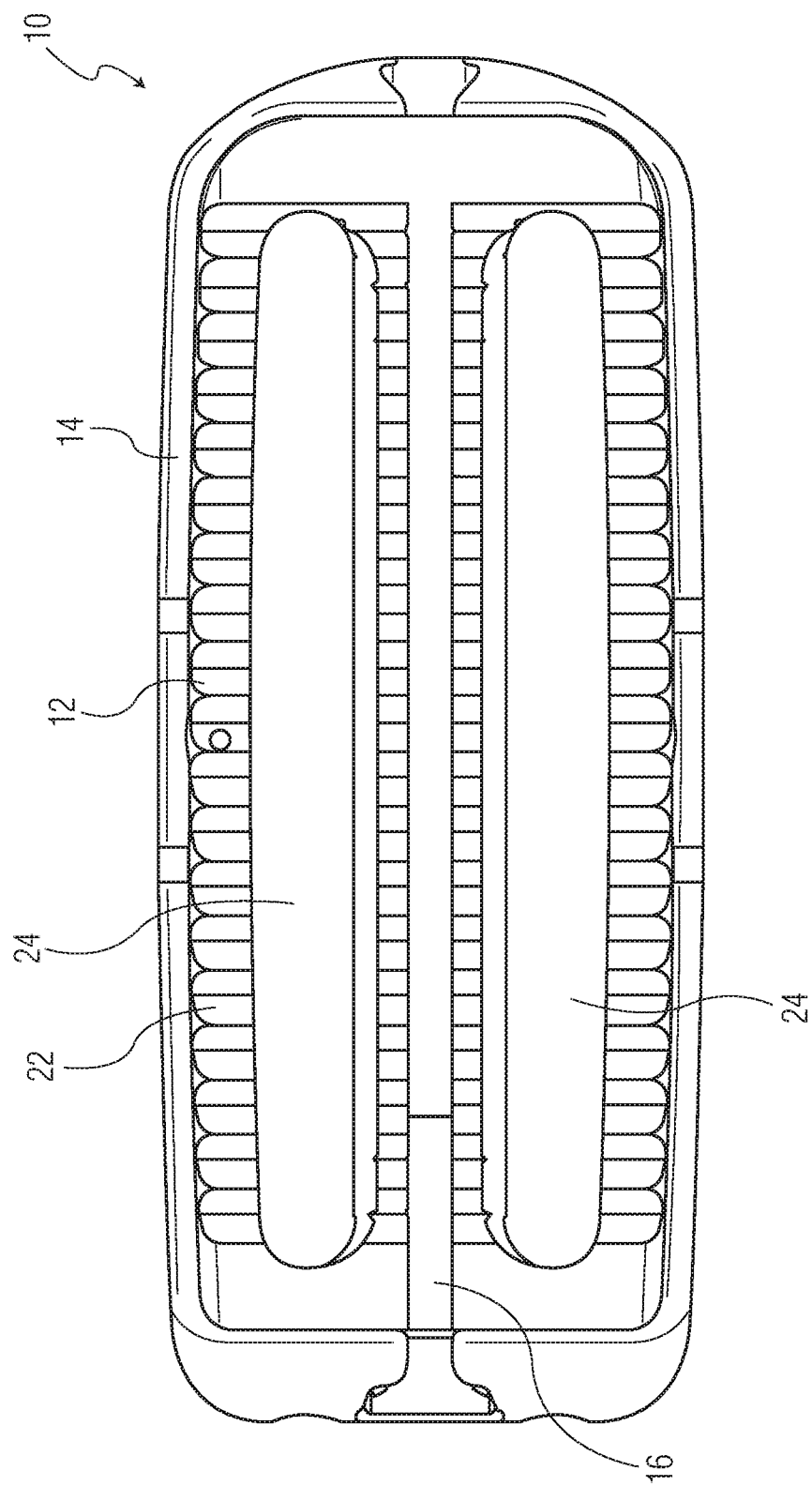
FIG. 2 is a top view of the implant of FIG. 1.
Figure 3:
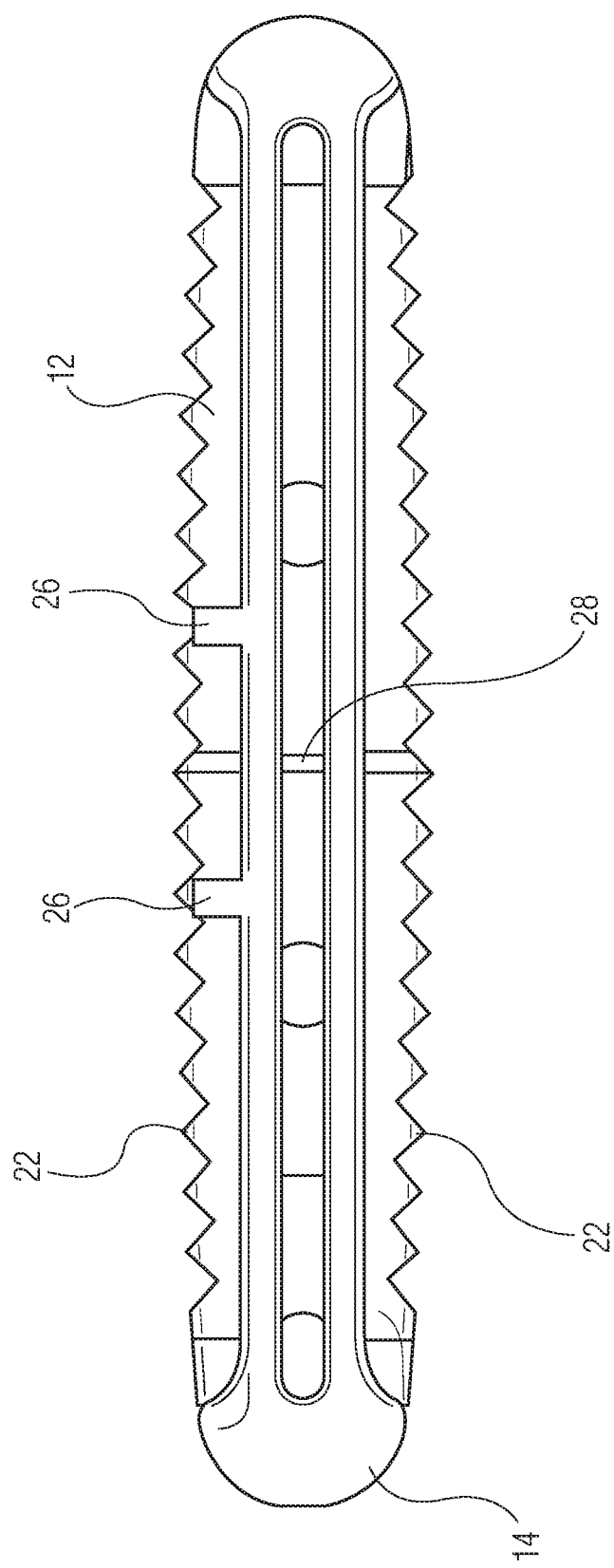
FIG. 3 is a side view of the implant of FIG. 1.
Figure 4:
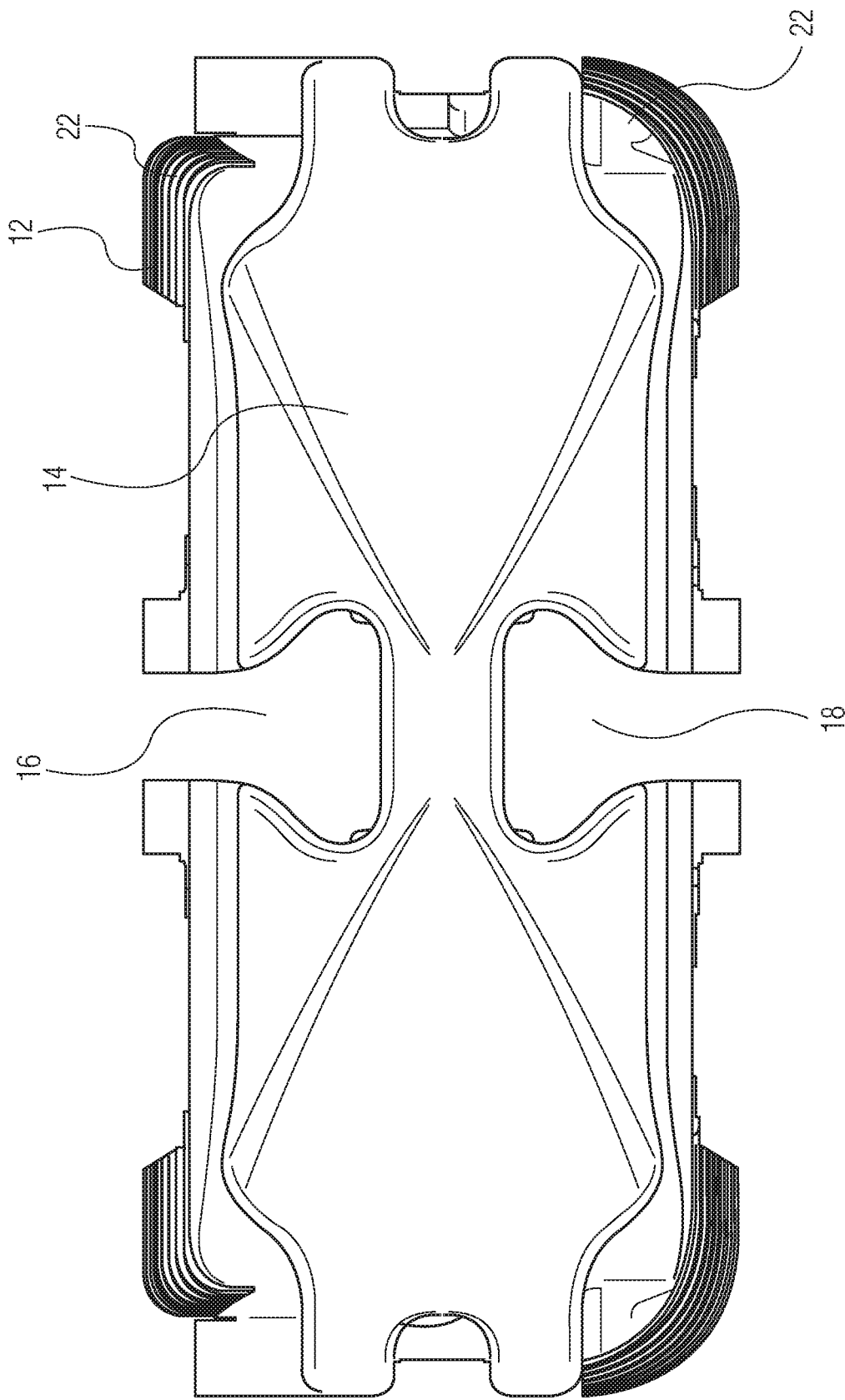
FIG. 4 is a front view of the implant of FIG. 1.

As shown in FIGS. 1-4, an implant 10 is disclosed that includes a PEEK body 12 and a metallic jacket 14. Jacket 14 is sized and shaped so as to fit around an exterior of PEEK body 12, and both components include portions of an upper channel 16 and a lower channel 18 (the latter of which is best shown in FIG. 4) that are designed to accept an anchor (like anchor 120 shown in FIG. 5). This design allows for implant 10 to be placed between adjacent intervertebral bodies and anchors to thereafter be secured to both the implant and the vertebral bodies, thereby creating a stand-alone fusion cage construct. In the particular embodiment shown in the figures of the present application, the various implants are designed for lateral placement between adjacent vertebral bodies. In other words, the implants are sized and shaped to be placed from the side of a patient and across the disc space. The particular lateral implants shown may exhibit lengths within the range of 40-60 mm, widths within the range of 18-22 mm and heights in the range of 8-18 mm. However, it is contemplated that the present invention has applicability to implants of many different sizes and shapes, including those designed for placement in other orientations, e.g., anteriorly, posteriorly, posterior-laterally or the like. Depending upon the particular insertion orientation, the implants may be sized within different ranges.

PEEK body 12 includes teeth 22 on and a plurality of apertures 24 through its top and bottom surfaces. The teeth aid in at least initially securing the implant between adjacent vertebral bodies, while the apertures may be packed with bone graft material to allow for bone to grow between the vertebral bodies. Of course, it is contemplated that the implant may be designed such that teeth are not included and/or one or more apertures may be provided. Moreover, although described as being constructed of PEEK, it is noted that body 12 may be constructed of many different materials, including many different polymeric materials in accordance with the present invention. It is also contemplated to construct body 12 of biologic materials, such as allograft bone.

Jacket 14, on the other hand, is comprised of a metallic material and designed such that it entirely surrounds PEEK body 12. Because jacket 14 is comprised of a metallic material, it can be seen when conducting an x-ray or other imaging technique. This is in contrast to the polymeric material of body 12, which cannot optimally be seen in such imaging procedures (PEEK can be seen depending upon x-ray settings). Jacket 14 is shown as including end portions separated by four rails (two on each side of the jacket), but can be of any shape sufficient to surround body 12.

Jacket 14 includes four extensions 26 (two on each side of the implant) which extend toward an upper surface of implant 10. Extensions 26 are shown as being equally spaced from ends of jacket 14, as well as about its center. Of course, extensions 26 may be positioned at any position on jacket 14. These structures provide specific reference points for a surgeon viewing implant 10 under an imaging process. For instance, a typical image will be taken from a front portion of a patient's body, and if implant 10 is correctly placed, extensions 26 on the front and back side of the implant will align such that only two extensions 26 will be visible in the image. However, when implant 10 is not properly aligned (e.g., rotated in one direction or the other), the image will begin to show extensions 26 on the posterior side of the implant (i.e., at least portions of all four extensions will show).

It is noted that other portions of jacket 14 may also aide in the determination of the placement of implant 10. For instance, the end portions of the implant (best shown on the left and right sides of the view of FIG. 3) can be utilized by a surgeon in a similar fashion to extensions 26. Likewise, the rails on the front and back of jacket 14 can be utilized to determine whether the implant is canted toward one of the upper or lower intervertebral body. This canting may occur because of subsidence, improper bone preparation or an improper placement. Extensions 26 are oriented so that they face the upper surface of implant 10. This allows for a quick determination as to whether the implant is properly oriented within the disc space. In other embodiments, extensions 26 could be oriented such that they face the bottom of the implant, or even to one side or the other. As is best shown in FIG. 3, body 12 may include its own radiopaque marker 28, which can be utilized in conjunction with extensions 26 to determine proper position of implant 10.

Of course, although described as being constructed of a metallic material, it is noted that jacket 14 may be constructed of many different types of materials, including different metals. In fact, the entirety of jacket 14 need not be radiopaque, although it is in the various embodiments of the present invention. Rather, extensions 26 may be the sole portion of jacket 14 constructed of radiopaque material, thereby allowing visualization during an imaging process.

Figure 5:
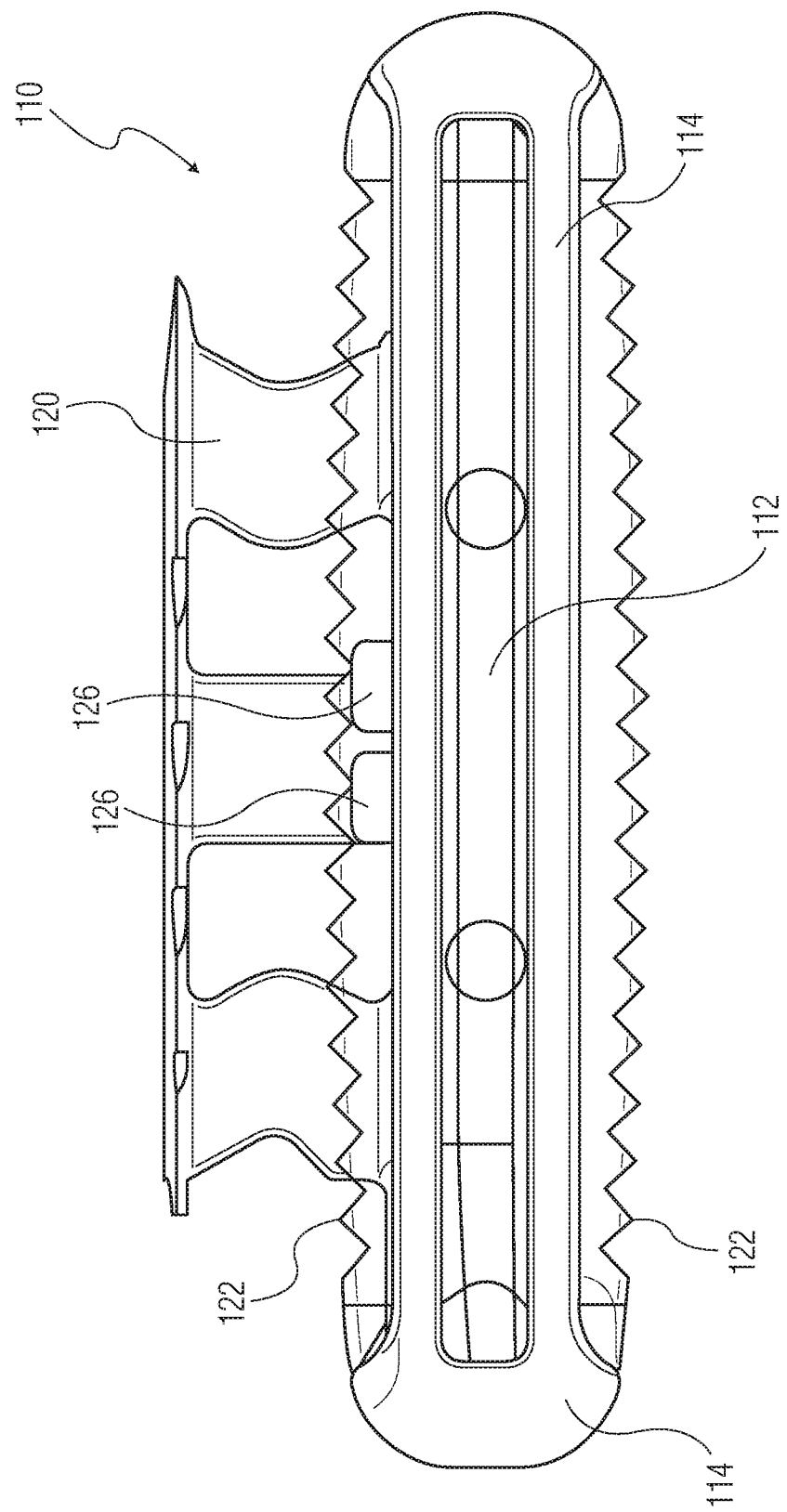
FIG. 5 is a side view of an implant according to another embodiment of the present invention.

FIGS. 5-13 disclose several additional embodiment implants in accordance with the present invention. For ease of reference, like reference numerals are utilized for similar elements of the implants, albeit within different 100-series of numbers. For instance, FIG. 5 depicts an implant 110 that includes a PEEK body 112, a jacket 114 and extensions 126. Extensions 126 are wider and include less of a distance therebetween than that of extensions 26 of implant. This design may allow for an easier determination of misalignment of implant 110, as the space between extensions 126 simply closes when viewed from the anterior side of the patient. Otherwise, extensions 126 are largely similar to those of implant 10.

Figure 6:
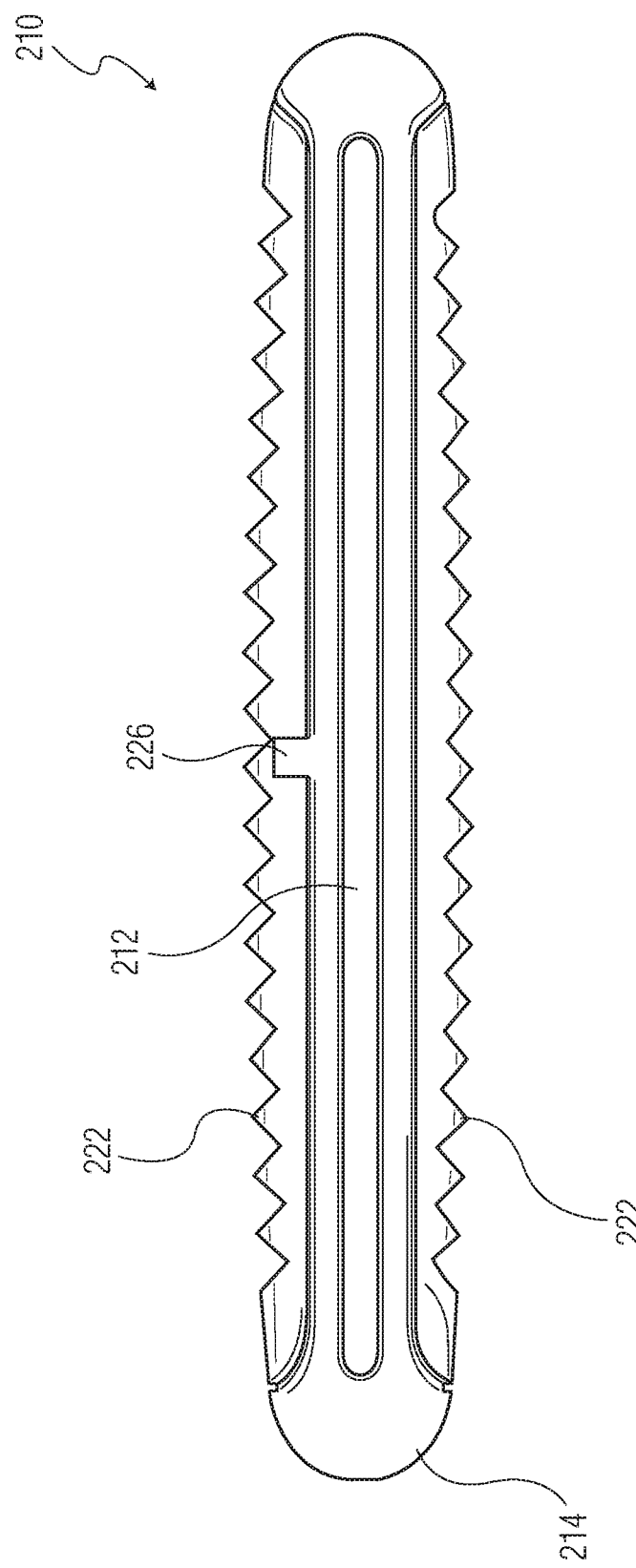
FIG. 6 is a side view of an implant according to another embodiment of the present invention.
Figure 7:
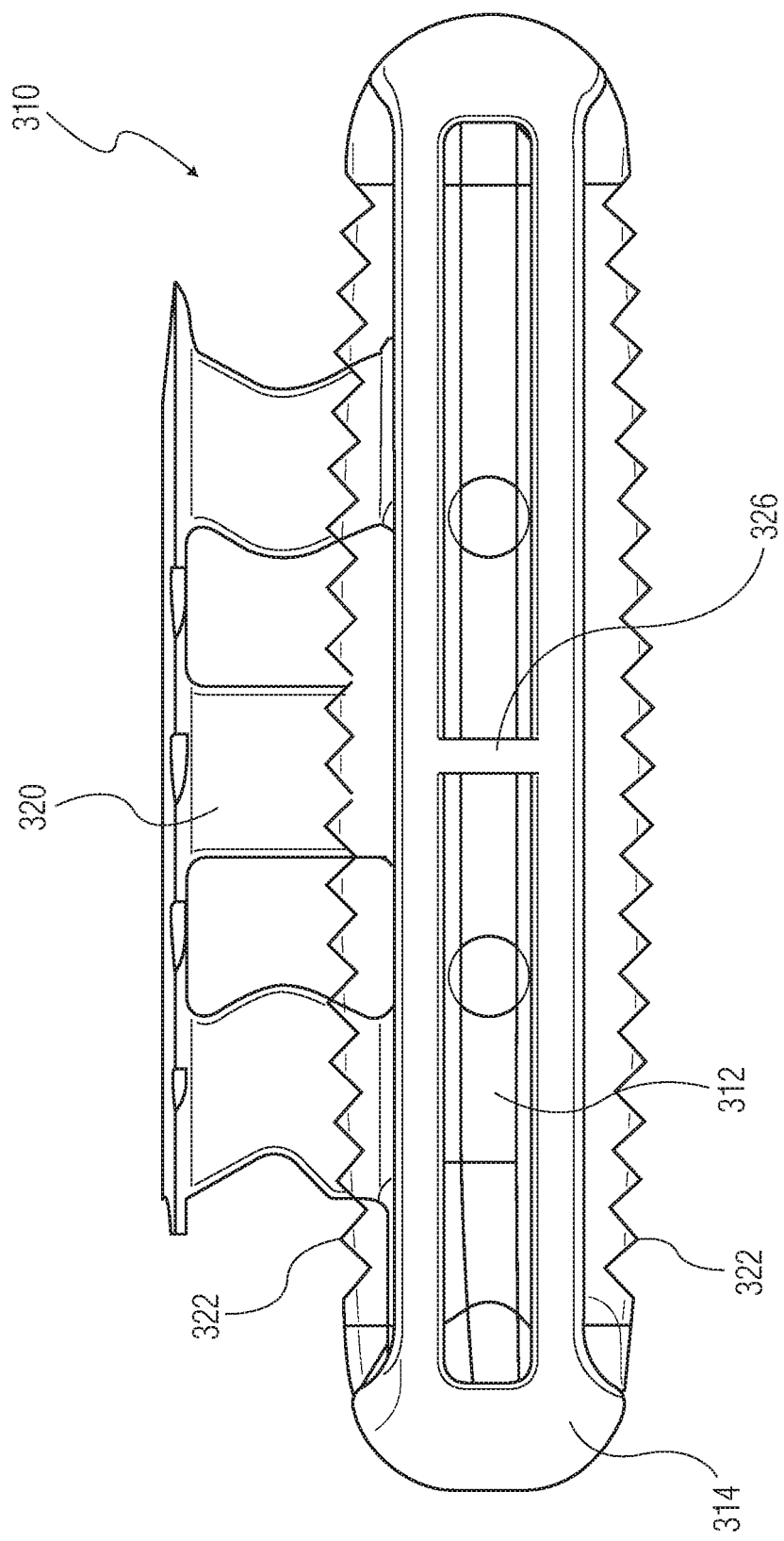
FIG. 7 is a side view of an implant according to another embodiment of the present invention.
Figure 8:
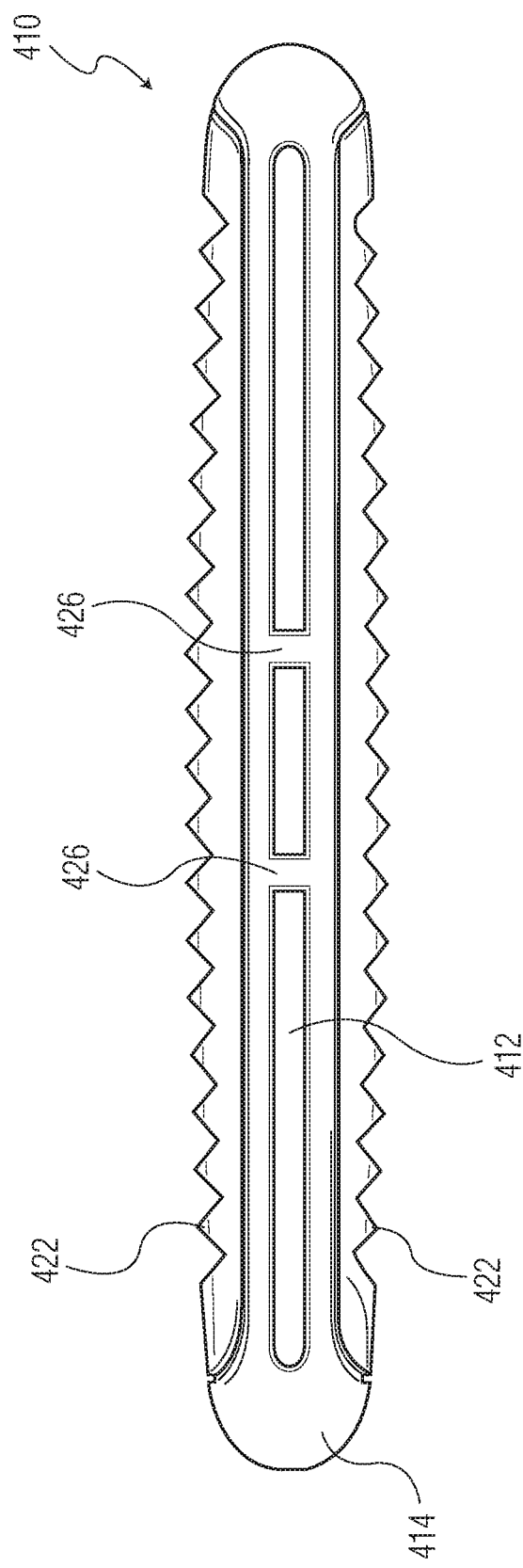
FIG. 8 is a side view of an implant according to another embodiment of the present invention.
Figure 9:
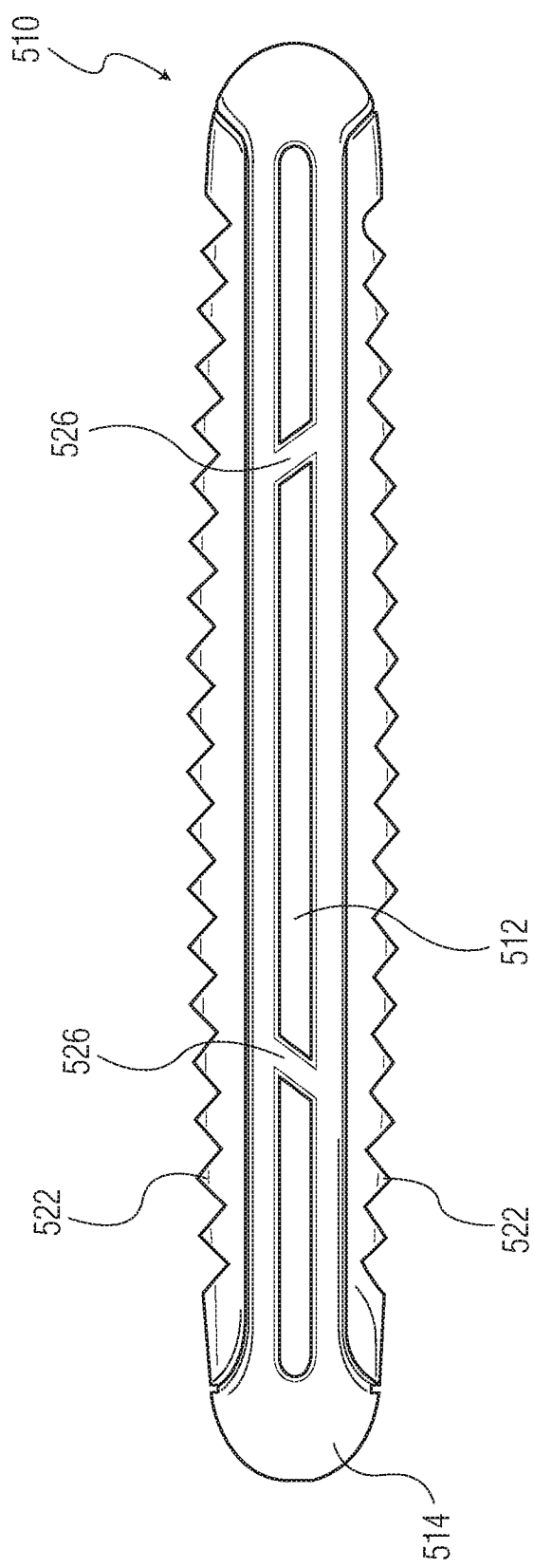
FIG. 9 is a side view of an implant according to another embodiment of the present invention.

Implant 210 of FIG. 6 includes a single extension 226 on each side. Therefore, instead of four extensions, implant 210 includes two. In the particular embodiment shown, extensions 226 are oriented at a center of implant 210, but could be positioned in other locations on jacket 214. FIG. 7 depicts an implant 310 in which extensions 326 extend between rails of jacket 314 on each side of the implant. This design not only provides a similar functionality to the foregoing implants, but also potentially adds stability to the construct of jacket 314. FIG. 8 depicts a design similar to implant 310, but with two extensions 426 extending between rails on both sides of the implant. Therefore, instead of the two extensions shown in FIG. 7, the embodiment of implant 410 includes four. Implant 510 of FIG. 9 includes four angled extensions 526 that extend between the rails. Again, the functionality of extensions 526 otherwise remains the same.

Figure 10:
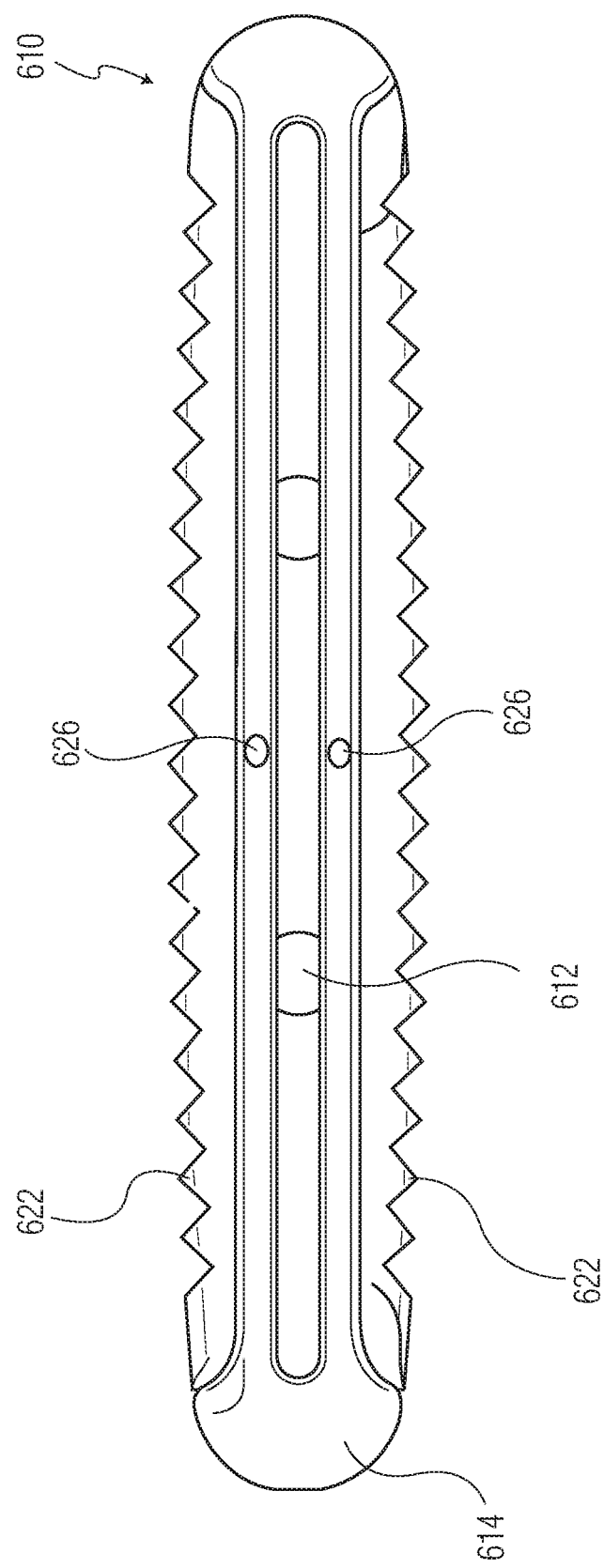
FIG. 10 is a side view of an implant according to another embodiment of the present invention.
Figure 11:
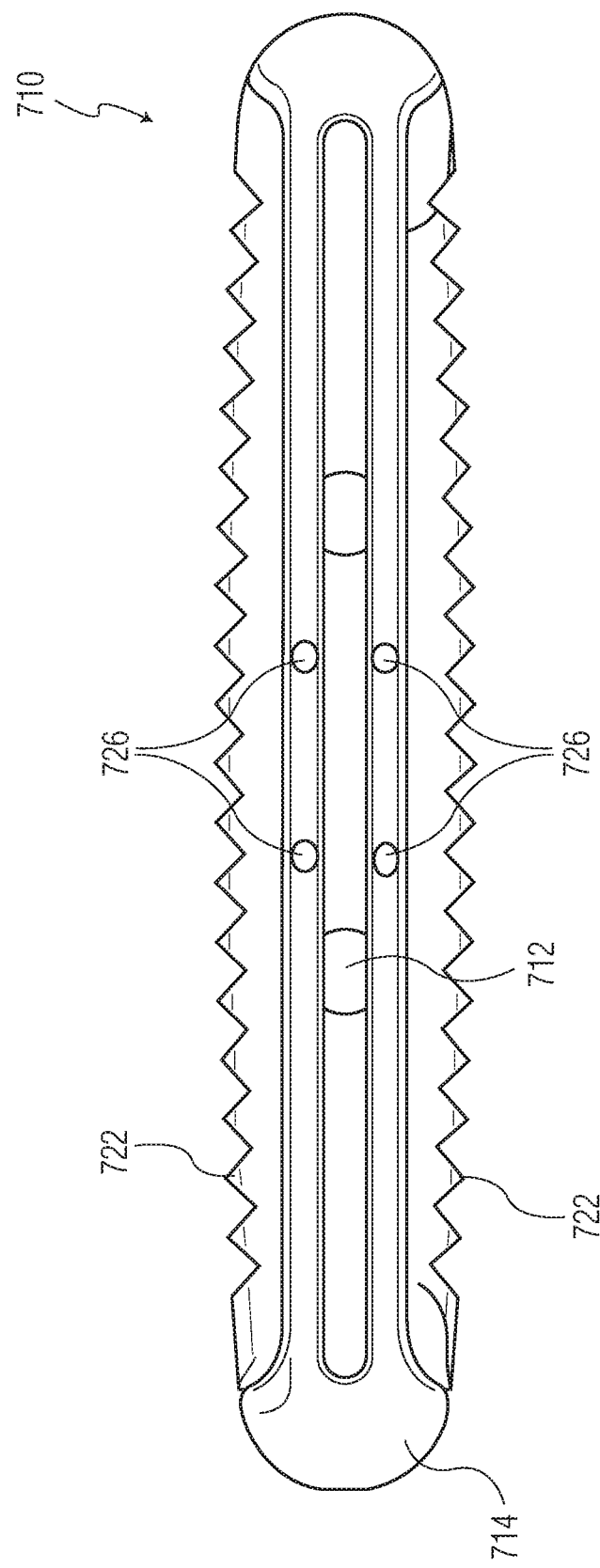
FIG. 11 is a side view of an implant according to another embodiment of the present invention.
Figure 12:
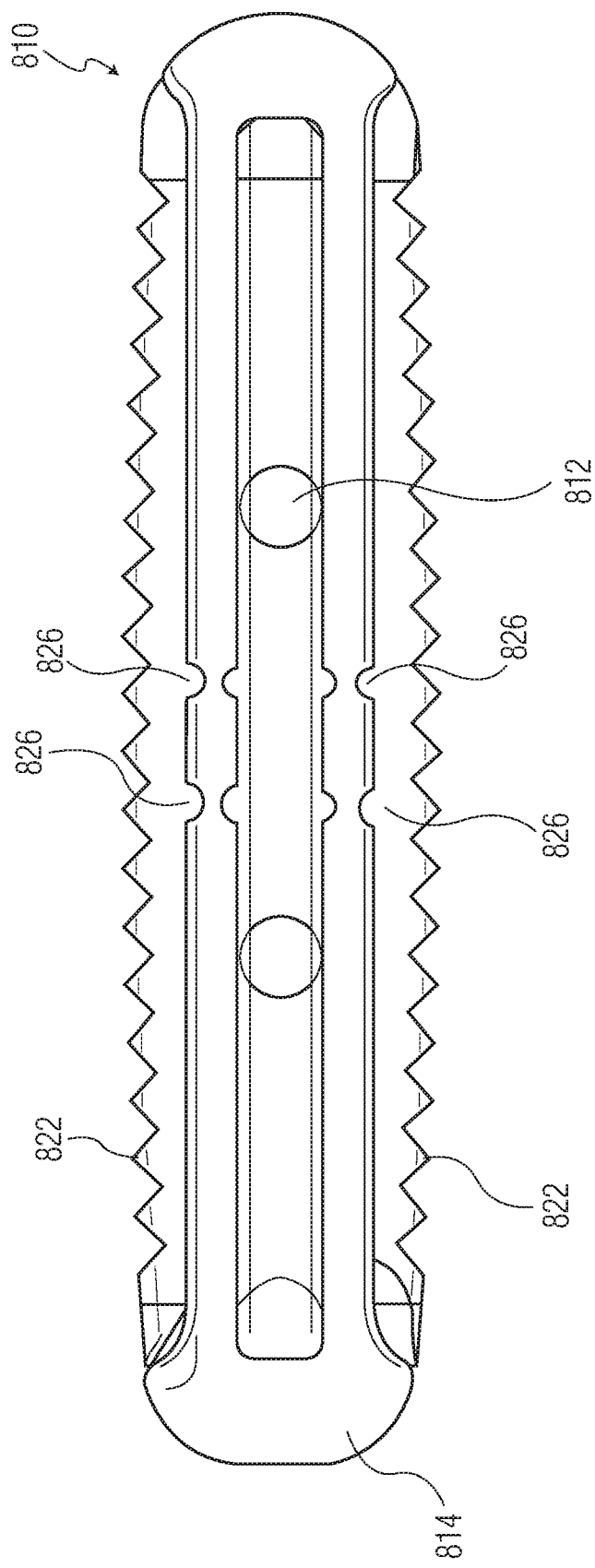
FIG. 12 is a side view of an implant according to another embodiment of the present invention.

FIG. 10 depicts an embodiment in which instead of extensions, jacket 614 includes holes 626 formed in the rails thereof. Holes 626 provide the surgeon with similar viewing capabilities in an imaging process as the above-discussed embodiments do. For instance, a properly placed implant will show two complete holes extending through the jacket, whereas a tilted or otherwise improperly placed implant will show the hole somewhat obscured. FIG. 11 depicts an embodiment in which eight holes 726 are included in jacket 714. FIG. 12 depicts a design in which instead of holes, jacket 814 includes necked down sections 826 that can be utilized in a similar fashion to the holes.

Figure 13:
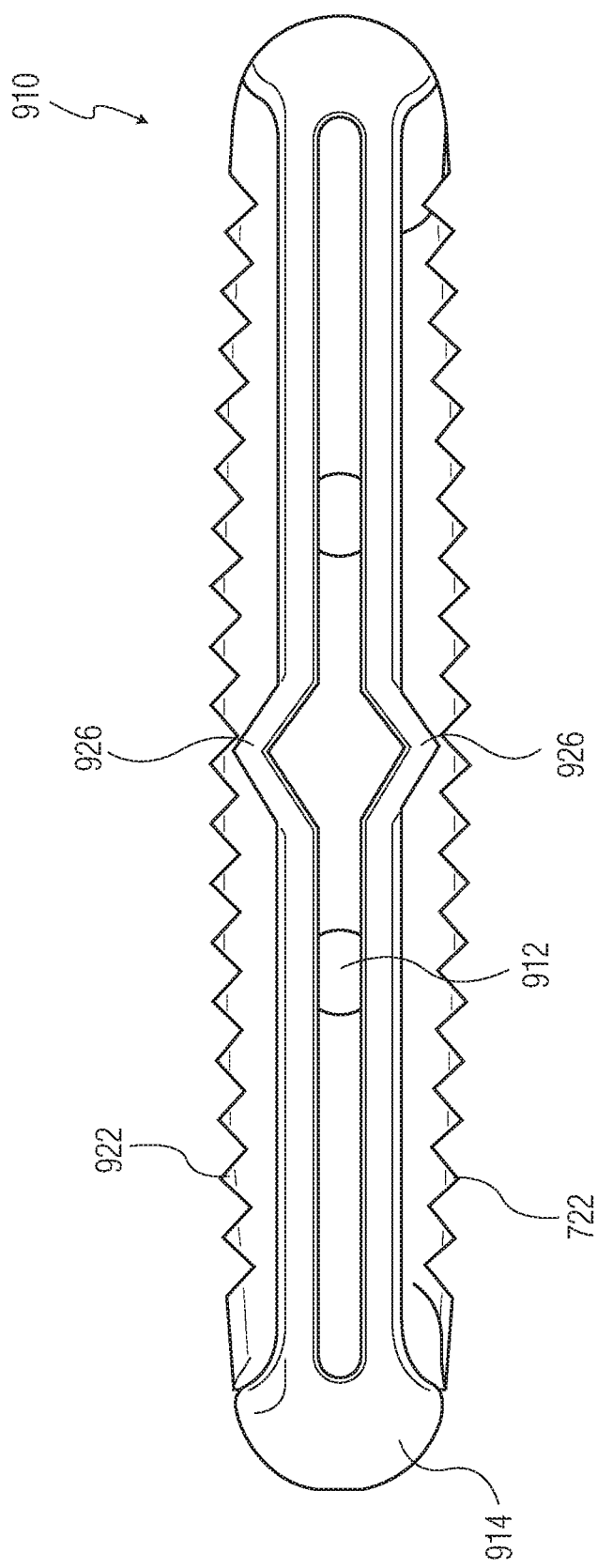
FIG. 13 is a side view of an implant according to another embodiment of the present invention.
Figure 14:
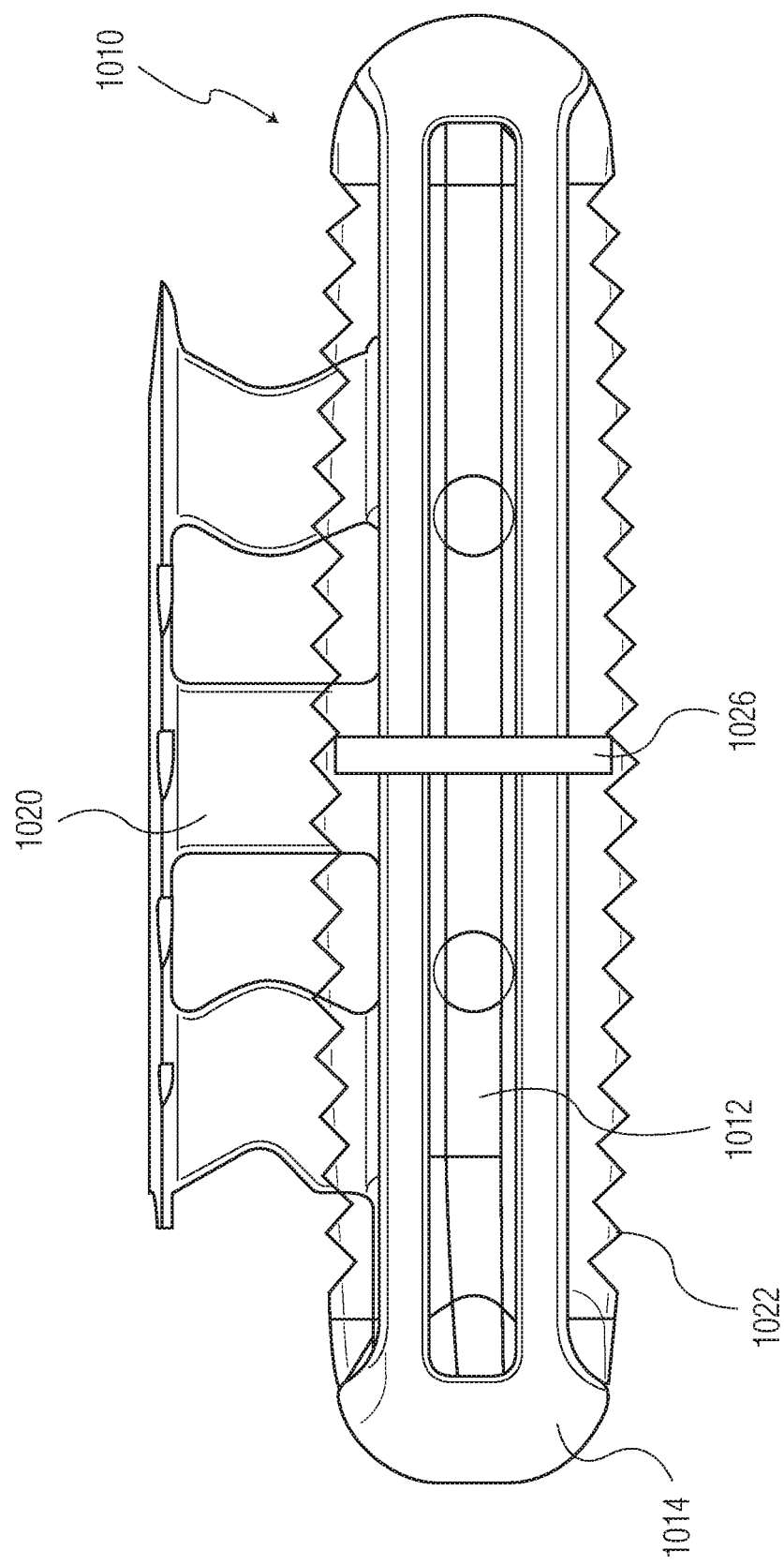
FIG. 14 is a side view of an implant according to another embodiment of the present invention.

Implant 910 of FIG. 13 includes triangular extensions 926 that can be utilized in a similar fashion as is discussed above in connection with implant 10. The triangular shape of extensions 926 allow for them to extend to a height on implant 910 that is possible with the above-discussed extensions. Moreover, the center area of extensions 926 allow for better visualization of the remainder of implant 910. This can be utilized to, among other things, better assess the amount of bone growth that has occurred through body 912 of an implanted implant 910. Finally, implant 1010 of FIG. 14 depicts and embodiment similar to that of FIG. 7. However, instead of extending towards only one of the upper or lower surface of the implant, extensions 1026 extend towards both. This design may allow for an easier determination of where those upper and lower surfaces are in an implanted implant.

In one embodiment of the invention, an intervertebral implant comprises:

a body sized and shaped for placement between first and second adjacent vertebrae;

a jacket disposed around the spacer; and at least two radiopaque markers extending from the jacket to enable identification of an orientation of the implant.

In another embodiment of the invention, a method of determining the orientation of an implant placed between two intervertebral bodies comprises the steps of:

viewing opposed radioactive markers located on front and back sides of a jacket of the implant; and determining the orientation of the implant based on the orientation of the markers, wherein in an aligned orientation, only a single marker is visible from a first aspect.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of determining the orientation of an implant between two vertebral bodies, comprising the steps of:
    viewing the implant from a first aspect;
    determining the orientation of the implant based on the orientation of a first hole located on a first side of the implant and a second hole located on a second side of the implant, the second hole opposing the first hole,
    wherein in an aligned orientation, both of the first and second holes are completely visible from the first aspect.

2. The method of claim 1, wherein in a misaligned orientation, neither of the first and second holes is completely visible from the first aspect.

3. The method of claim 2, wherein the first aspect is from an anterior side of a patient.

4. The method of claim 1, wherein the implant includes a jacket surrounding a body, the body being at least partially radiopaque.

5. The method of claim 1, further comprising a third hole located on the first side of the implant and a fourth hole located on the second side of the implant, the fourth hole opposing the third hole.

6. The method of claim 5, wherein in the aligned orientation, both of the third and fourth holes are visible from the first aspect.

7. The method of claim 1, wherein the step of determining includes determining the orientation of the implant based on the orientation of the first hole placed on a first rail on the first side of the implant and the second hole placed on a second rail on the second side of the implant.

8. The method of claim 1, further comprising the step of securing the implant to at least one of the two vertebral bodies using at least one anchor.

9. The method of claim 1, further comprising the step of securing the implant to the vertebral bodies using teeth extending from bottom and top surfaces of the implant.

10. A method of determining the orientation of an implant between two vertebral bodies, comprising the steps of:
    viewing the implant from a first aspect, the implant including a jacket surrounding a body, the body being partially radiopaque;
    determining the orientation of the implant based on the orientation of a first necked down portion located on a first side of the implant and a second necked down portion located on a second side of the implant, the second necked down portion opposing the first necked down portion,
    wherein in an aligned orientation, only one of the first and second necked down portions is visible from the first aspect.

11. The method of claim 10, wherein in a misaligned orientation, neither of the first and second necked down portions is completely visible from the first aspect.

12. The method of claim 11, wherein the first aspect is from an anterior side of a patient.

13. The method of claim 10, further comprising a third necked down portion located on the first side of the implant and a fourth necked down portion located on the second side of the implant, the fourth necked down portion opposing the third necked down portion.

14. The method of claim 13, wherein in the aligned orientation, one of the third and fourth necked down portions is visible from the first aspect.

15. The method of claim 10, wherein the step of determining includes determining the orientation of the implant based on the orientation of the first necked down portion placed on a first rail on the first side of the implant and the second necked down portion placed on a second rail on the second side of the implant.

16. The method of claim 10, further comprising the step of securing the implant to at least one of the two vertebral bodies using at least one anchor.

17. The method of claim 10, further comprising the step of securing the implant to the vertebral bodies using teeth extending from bottom and top surfaces of the implant.

18. A method of determining the orientation of an implant between two vertebral bodies, comprising the steps of:
    viewing the implant from a first aspect, the implant being at least partially radiopaque, determining the orientation of the implant based on the orientation of a first hole having a first circumference and being located on a first side of the implant, a second hole having a second circumference and being located on a second side of the implant, the second hole opposing the first hole, wherein in an aligned orientation, the first circumference and the second circumference completely overlap when viewed from the first aspect.

19. The method of claim 18, wherein in a misaligned orientation, neither of the first and second holes is completely visible from the first aspect.

20. The method of claim 18, wherein the step of determining includes determining the orientation of the implant based on the orientation of the first hole placed on a first rail on the first side of the implant and the second hole placed on a second rail on the second side of the implant.

* * * * *